(12) United States Patent
Verespej et al.

(10) Patent No.: US 10,702,663 B2
(45) Date of Patent: Jul. 7, 2020

(54) RECONSTITUTION MEANS FOR SAFETY DEVICE

(71) Applicant: Safety Syringes, Inc., Franklin Lakes, NJ (US)

(72) Inventors: James M. Verespej, San Marcos, CA (US); Philip E. Dowds, San Diego, CA (US)

(73) Assignee: Safety Syringes, Inc., Franklin Lakes, NJ (US)

( * ) Notice: Subject to any disclaimer, the term of this patent is extended or adjusted under 35 U.S.C. 154(b) by 25 days.

(21) Appl. No.: 15/293,912

(22) Filed: Oct. 14, 2016

(65) Prior Publication Data

US 2017/0028139 A1 Feb. 2, 2017

Related U.S. Application Data

(63) Continuation of application No. 13/363,168, filed on Jan. 31, 2012, now Pat. No. 9,498,581, which is a
(Continued)

(51) Int. Cl.
*A61M 5/32* (2006.01)
*A61M 5/178* (2006.01)
(Continued)

(52) U.S. Cl.
CPC .......... *A61M 5/326* (2013.01); *A61M 5/1782* (2013.01); *A61M 5/31505* (2013.01);
(Continued)

(58) Field of Classification Search
CPC ........ A61M 2205/276; A61M 2205/27; A61M 2205/273; A61M 2005/2073;
(Continued)

(56) References Cited

U.S. PATENT DOCUMENTS 3,548,824 A 12/1970 Carr
4,060,082 A 11/1977 Lindberg et al.
(Continued)

FOREIGN PATENT DOCUMENTS

EP 0467173 A1 1/1992
FR 2861310 A1 4/2005
(Continued)

OTHER PUBLICATIONS

Instructions for Use for Bio-Set Injection from Bio-Set Website, printed Jan. 14, 2003 (http://www.bio-set.com/htm/InstUseInj.htm).
(Continued)

*Primary Examiner* — Amber R Stiles
(74) *Attorney, Agent, or Firm* — The Webb Law Firm (57) ABSTRACT

The present disclosure describes a needle guard device or system that can be used with drugs requiring reconstitution. The needle guard is preferably a passive needle guard that can be used during reconstitution without activating the safety mechanism. Following administration of the medication, the needle guard shields a user from inadvertent needle sticks by extending a protective shield over the needle.

15 Claims, 8 Drawing Sheets

Related U.S. Application Data continuation of application No. 12/368,604, filed on Feb. 10, 2009, now Pat. No. 8,105,292.

(60) Provisional application No. 61/027,742, filed on Feb. 11, 2008.

(51) Int. Cl.
*A61M 5/315* (2006.01)
*A61M 5/20* (2006.01)
*A61M 5/31* (2006.01)

(52) U.S. Cl.
CPC .............. *A61M 2005/2073* (2013.01); *A61M 2005/3114* (2013.01); *A61M 2005/3247* (2013.01); *A61M 2005/3261* (2013.01); *A61M 2005/3264* (2013.01)

(58) Field of Classification Search
CPC .......... A61M 2005/3247; A61M 5/326; A61M 5/1782; A61M 5/31505; A61M 2005/3114; A61M 2005/3261; A61M 2005/3264
See application file for complete search history.

(56) References Cited

U.S. PATENT DOCUMENTS

| | | |
|---|---|---|
| 4,919,657 A | 4/1990 | Haber et al. |
| 5,201,708 A | 4/1993 | Martin |
| 5,279,583 A | 1/1994 | Shober, Jr. et al. |
| 5,320,603 A | 6/1994 | Vetter et al. |
| 5,324,265 A | 6/1994 | Murray et al. |
| 5,389,085 A | 2/1995 | D'Alessio et al. |
| 5,569,193 A | 10/1996 | Hofstetter et al. |
| 5,591,138 A | 1/1997 | Vaillancourt |
| 5,779,668 A | 7/1998 | Grabenkort |
| 5,785,682 A | 7/1998 | Grabenkort |
| 5,971,953 A | 10/1999 | Bachynsky |
| 5,976,111 A | 11/1999 | Hart |
| 6,149,623 A | 11/2000 | Reynolds |
| 6,186,980 B1 | 2/2001 | Brunel |
| 6,253,804 B1 | 7/2001 | Safabash |
| 6,332,876 B1 | 12/2001 | Poynter et al. |
| 6,364,865 B1 | 4/2002 | Lavi et al. |
| 6,379,336 B1 | 4/2002 | Asbaghi et al. |
| 6,419,658 B1 | 7/2002 | Restelli et al. |
| 6,440,101 B1 | 8/2002 | Grabenkort et al. |
| 6,474,369 B2 | 11/2002 | Castellano |
| 6,478,771 B1 | 11/2002 | Lavi et al. |
| 6,623,459 B1 | 9/2003 | Doyle |
| 6,656,163 B1 | 12/2003 | Marshall et al. |
| 6,729,370 B2 | 5/2004 | Norton et al. |
| 6,776,777 B2 | 8/2004 | Barrelle |
| 6,869,415 B2 | 3/2005 | Asbaghi |
| 6,939,330 B1 | 9/2005 | McConnell-Montalvo et al. |
| 7,118,552 B2 | 10/2006 | Shaw et al. |
| 7,140,401 B2 | 11/2006 | Wilcox et al. |
| 7,207,973 B2 | 4/2007 | Barrelle |
| 7,294,119 B2 | 11/2007 | Westbye et al. |
| 7,314,464 B2 | 1/2008 | Giambattista et al. |
| 9,044,378 B2 | 6/2015 | Verespej et al. |
| 2005/0027255 A1* | 2/2005 | Lavi ................... A61M 5/2033 604/135 |
| 2005/0277894 A1 | 12/2005 | Westbye et al. |
| 2006/0036217 A1 | 2/2006 | Doyle |
| 2006/0111679 A1 | 5/2006 | Millerd |
| 2007/0179441 A1 | 8/2007 | Chevallier |
| 2007/0265576 A1* | 11/2007 | Pessin ................. A61M 5/3202 604/198 |
| 2008/0015513 A1 | 1/2008 | Westbye et al. |

FOREIGN PATENT DOCUMENTS

| | | | |
|---|---|---|---|
| GB | 2079607 A | 1/1982 | |
| WO | 9300949 A1 | 1/1993 | |
| WO | 9531235 A1 | 11/1995 | |
| WO | 0145776 A1 | 6/2001 | |
| WO | 02072182 A1 | 9/2002 | |
| WO | 02076542 A1 | 10/2002 | |
| WO | 2004045685 A1 | 6/2004 | |
| WO | 2007144507 A1 | 12/2007 | |
| WO | WO 2007144507 A1 * | 12/2007 | ............ A61M 5/326 |
| WO | WO-2007144507 A1 * | 12/2007 | ............ A61M 5/326 |

OTHER PUBLICATIONS

Press Release from PR Web Website entitled "Second Patent for Mixing Lyophilized (Freeze-Dried) Drugs in a Needle-Less Injector Awarded to Penject® Corporation", printed Jan. 14, 2003 (http://www.prweb.com/printer.php?prid=31822).

Pre-Filled Diluent and Pre-filled Drug Syringes, printed Jan. 4, 2003 (http://www.baxterdrugdelivery.com/deliverysystems/syringes.html) (2 pages).

* cited by examiner

RECONSTITUTION MEANS FOR SAFETY DEVICE

CROSS-RELATIONSHIP TO PENDING APPLICATION

This application is a continuation of U.S. patent application Ser. No. 13/363,168 filed Jan. 31, 2012, which is a continuation of U.S. patent application Ser. No. 12/368,604 filed Feb. 10, 2009, now U.S. Pat. No. 8,105,292, which claims priority to U.S. Provisional Application Ser. No. 61/027,742 filed Feb. 11, 2008, the entire disclosures of each of which are incorporated herein by reference.

FIELD

This invention relates generally to syringe systems and methods for mixing and delivering a therapeutic agent formed by combining a diluent with a lyophilized drug or a concentrated drug. More specifically, this invention relates to syringe systems, including a passive needle guard, used for reconstitution of lyophilized or concentrated drugs and methods for using such systems.

BACKGROUND

Lyophilization is a process by which the volatile components of a drug are removed in order to extend the shelf-life of the medication. Lyophilization may involve the rapid freezing of a material at a very low temperature followed by rapid dehydration. Solvents such as water are removed from the drug yielding a substance that is more stable and can be stored. Lyophilized drugs are generally stored in a glass vial or cartridge and covered by a rubber stopper or septum.

In order to administer the lyophilized drugs, the drug must generally be reconstituted. Reconstitution is the process of hydrating drugs that are packaged and stored in a dry lyophilized state. A diluent, such as water, saline, 5% Aqueous Dextrose or the like, is added to the lyophilized drug and the combination is mixed until the drug is fully dissolved. A syringe is typically used to inject the diluent into the vial containing the lyophilized drug. The syringe may be pre-filled with the diluent or the user may first withdraw the diluent from a second vial or container into the syringe. After the diluent is added to the vial containing the lyophilized drugs, the contents are then mixed to form a therapeutic agent.

After complete mixing of the diluent and the lyophilized drug, the therapeutic agent may be aspirated back into the syringe. Once the therapeutic agent is in the syringe, the medication is administered to the patient. Usually the therapeutic agent is administered within a short time after reconstitution in order to ensure that the drug is not degraded by the solvent.

Most current systems for reconstitution expose the user to the risk of inadvertent needle sticks. In addition, current systems may not adequately prevent the possible reuse of the syringe. A number of needle guards for syringes have been developed that are intended to prevent accidental needle sticks and/or inadvertent reuse of a syringe. However, because syringe safety shield devices normally actuate when the plunger is fully advanced during the administration of the drug, these same devices will prematurely actuate the safety shield during the drug reconstitution phase as the diluent is added to the lyophilized drug. Therefore, a method for preventing the activation of the safety shield during drug reconstitution is highly desirable.

Accordingly, a syringe system that can be used for reconstitution and that would automatically activate a needle shield during or following administration of the therapeutic agent would be considered useful.

SUMMARY

The present invention is directed to a syringe system for reconstitution of lyophilized or concentrated drugs. The present invention is also directed to the combination of such a system with a passive needle guard that is automatically activated to extend a shield to cover a needle of the syringe and to methods of making and using such systems. Typically, a passive needle guard shield is activated when a radial portion or thumb pad of a plunger contacts a lateral catch or trigger finger of the passive needle guard. As the thumb pad of the plunger is moved distally, the trigger finger is forced laterally which results in a shield being forced distally to cover a needle of the syringe or in some designs, the syringe needle withdraws into the shield.

The present disclosure describes a needle guard device or system that can be used with drugs requiring reconstitution without activating the safety mechanism, yet provides needle safety shielding after the drug has been injected into the patient. In a preferred embodiment, the needle guard device would be assembled and sold with a syringe that is preferably pre-filled with the diluent. In a preferred embodiment, a clip is coupled to the needle guard during the reconstitution phase. The clip is configured to interact with the needle guard such that the shield is not activated to the extended position when the thumb pad of the plunger contacts the trigger fingers. Following reconstitution, the clip can be removed and the reconstituted medicine can be administered to the patient. During administration, the shield of the needle guard can be activated to extend and cover the needle.

DETAILED DESCRIPTION

Figure 1:
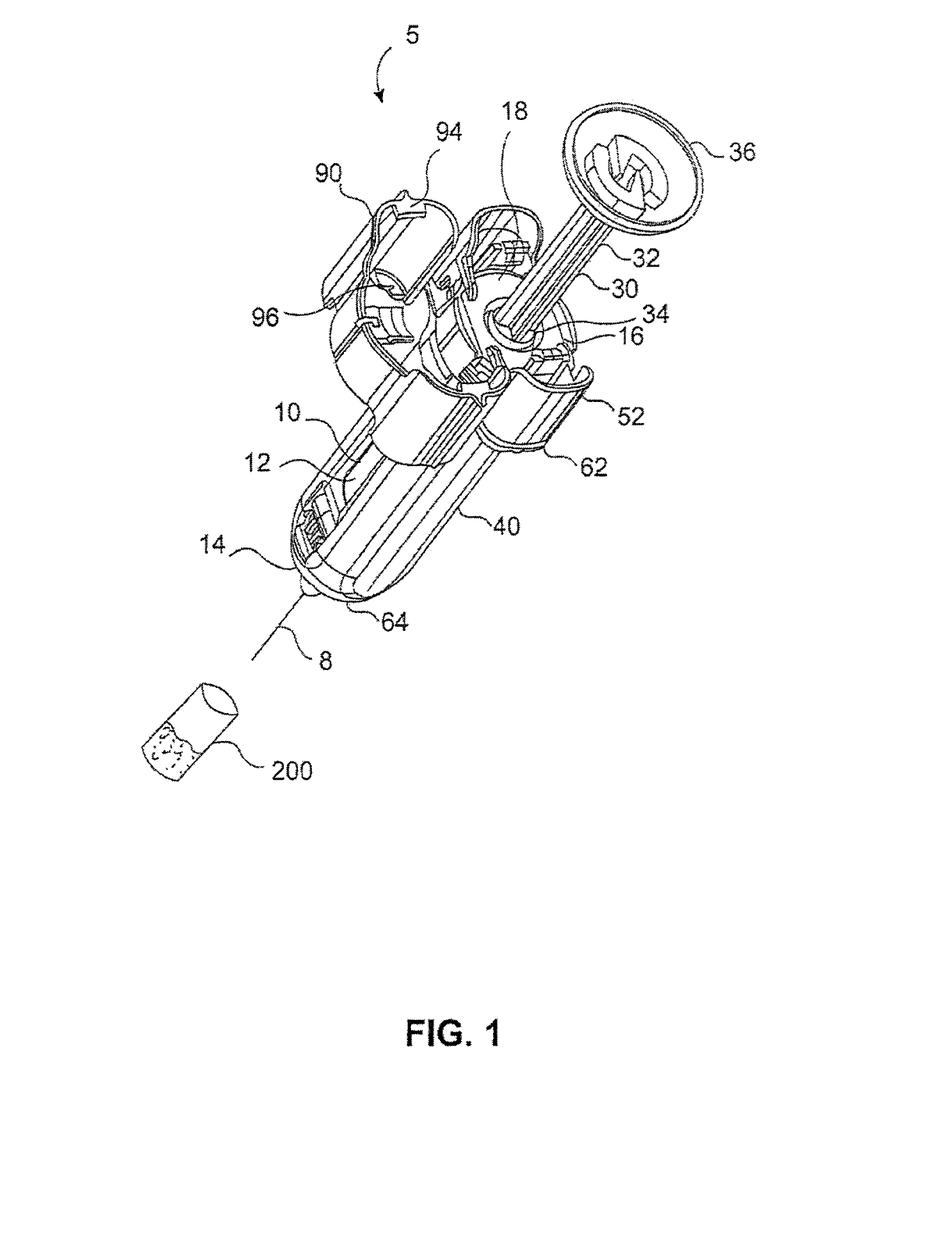
FIG. 1 shows an unassembled version of an exemplary embodiment of the device depicting the drug vial, clip, plunger, and the needle guard with an installed syringe.
Figure 2:
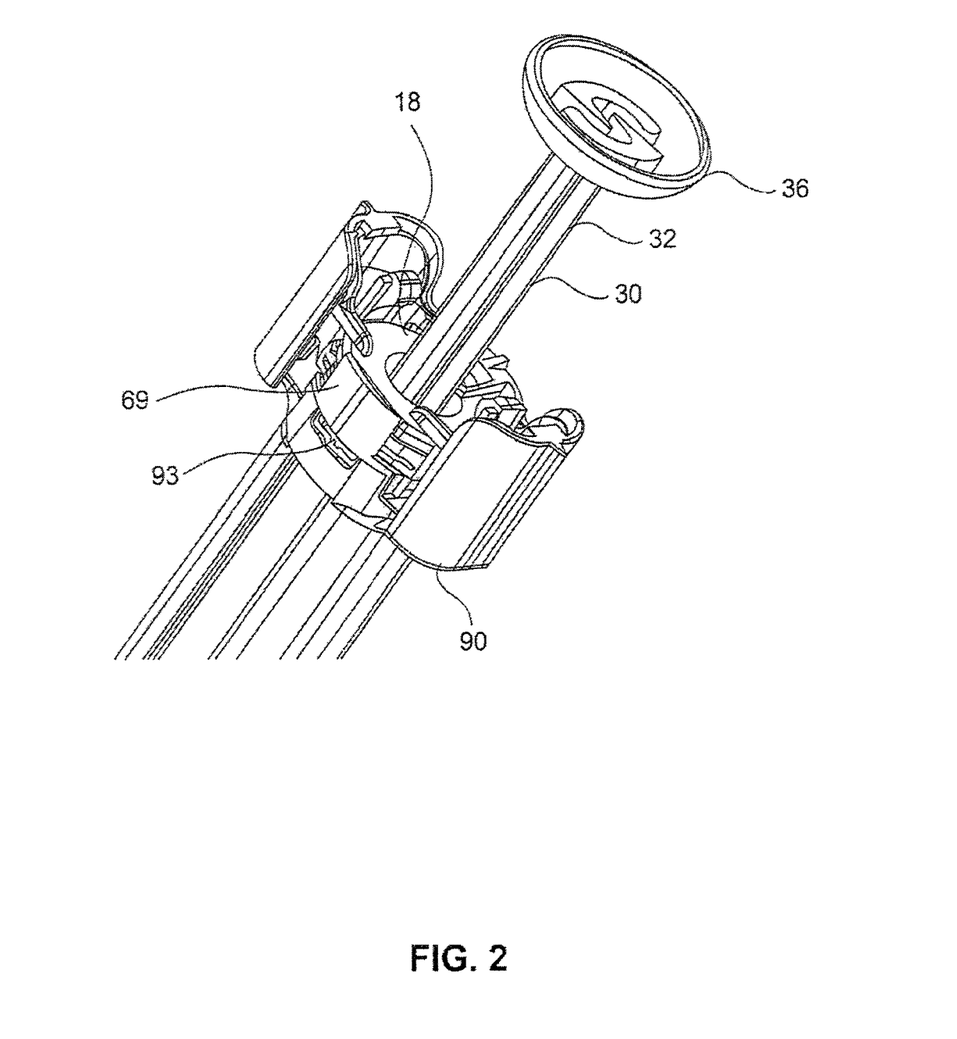
FIG. 2 shows an exemplary embodiment wherein the clip is attached to the proximal portion of the needle guard.

Turning to the figures, FIG. 1 depicts an exemplary embodiment of the present needle safety guard device 5 and related components in an unassembled arrangement. As will be discussed in greater detail herein, FIG. 1 shows a drug vial 200, needle guard 40 housing a syringe 10, clip 90, and plunger 30. In FIG. 1, the clip 90 is shown separated from the rest of the safety device to better illustrate the features of the clip 90, however, in a preferred embodiment the clip 90 is connected to the main part of the safety device 5 as shown in FIG. 2.

In accordance with one aspect of the present disclosure, a medicine cartridge, such as a syringe 10 is provided (FIG. 1). Preferably, the syringe 10 has a substantially smooth-walled cylindrical barrel 12, a hub or distal end 14 that is the administration end, and a proximal end 16 having a flange 18. The cylindrical barrel 12 typically is manufactured from substantially clear glass. Alternatively, the barrel 12 may be manufactured from plastic, e.g., polypropylene, k-resin, or polycarbonate, and the like.

The barrel 12 of the syringe 10 may be pre-filled with a diluent, or may be filled with the diluent at a later step. Preferably the syringe 10, if pre-filled, also comprises a label or markings that indicates the quantity and type of diluent. For example, a sticker or label may be attached to the barrel 12 of the syringe 10 which provides the name of the diluent and the volume of the diluent. The diluent may be of any type known in the art including, but not limited to, sterile water, saline, 5% Aqueous Dextrose or the like. Alternatively, the user may aspirate the diluent into the syringe from a vial or container.

Figure 7:
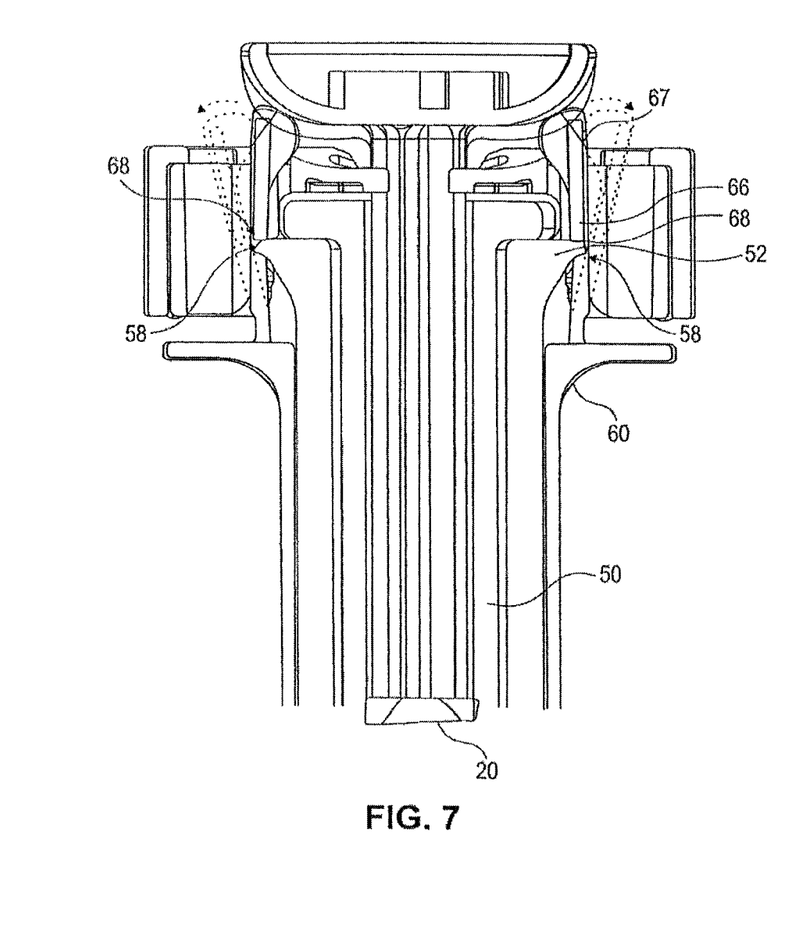
FIG. 7 shows a profile sectional view of the proximal portion of the needle guard with the clip removed. The dotted outline of the shield trigger fingers are shown in the unlatched position. The unlatched position is created when the plunger advances distally to an extent that the curved undersurface of the thumb pad pushes against the trigger fingers and displaces them laterally such that the latch surfaces of the shield trigger fingers and body are no longer engaged and will allow the shield to move distally with respect to the body unless prevented by the clip.

The proximal end 16 of the barrel 12 is configured to receive a stopper 20 and a plunger 30 (FIGS. 1 and 7). The stopper 20 is configured to be slidably coupled into the cylindrical barrel 12 and movable from a proximal position to a distal position. The stopper 20 is preferably made of pliable rubber, thermoplastic rubber, plastic or similar material. The plunger 30 comprises a stem 32, a distal end 34, and a radial portion or thumb pad 36 (FIG. 1). The plunger 30 is generally made of plastic, e.g. polypropylene, k-resin, or polycarbonate, or the like.

The distal end 14 of the cylindrical barrel 12 preferably comprises a needle port or Luer fitting (FIG. 1). The Luer fitting may be configured to couple with several different sizes of needles with different diameters and lengths or with other components that include a Luer fitting or other type of holder. The needles and components may be connected by a Luer connector, Luer slip, Luer, or other holder as is known in the art. The Luer fitting can be either of the slip version (no threads) or include threads. The Luer fitting is configured to allow interchanging of the needle and/or components so a user may use the most appropriate needle or component during filling the syringe, reconstitution, and administration of the medication to a patient.

Figure 5:
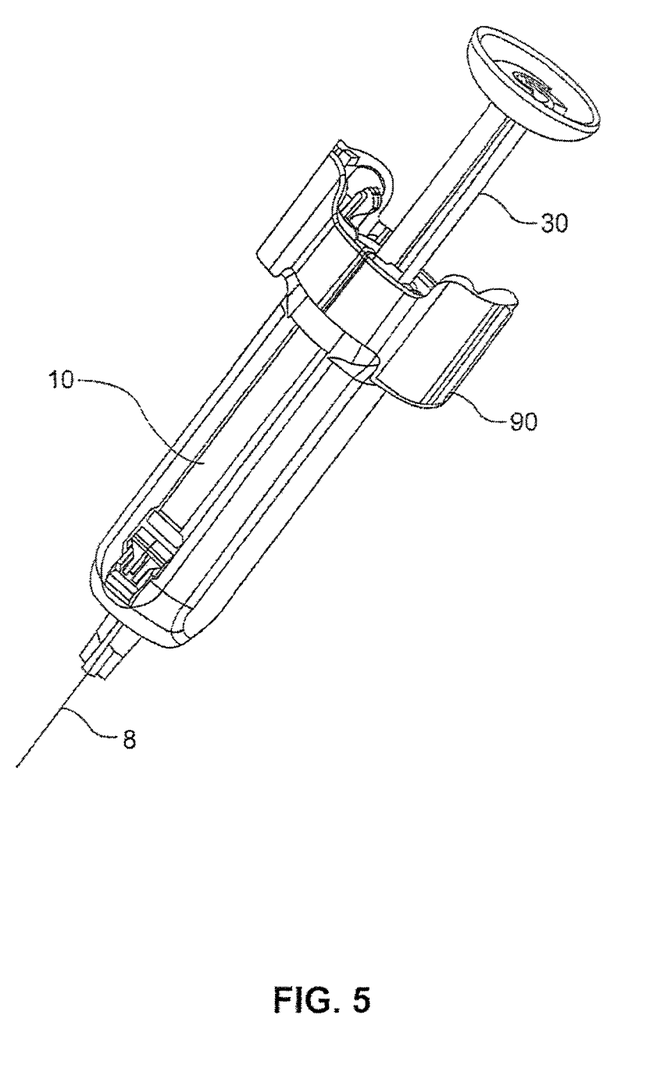
FIG. 5 shows an exemplary embodiment of the device with a reconstitution needle attached.

A first needle or reconstitution needle 8 can be attached to the Luer fitting (FIG. 5). The reconstitution needle 8 is preferably used during reconstitution and then replaced by a second, administration needle 15 (FIGS. 6 and 8) prior to administration of the medication.

Figure 8:
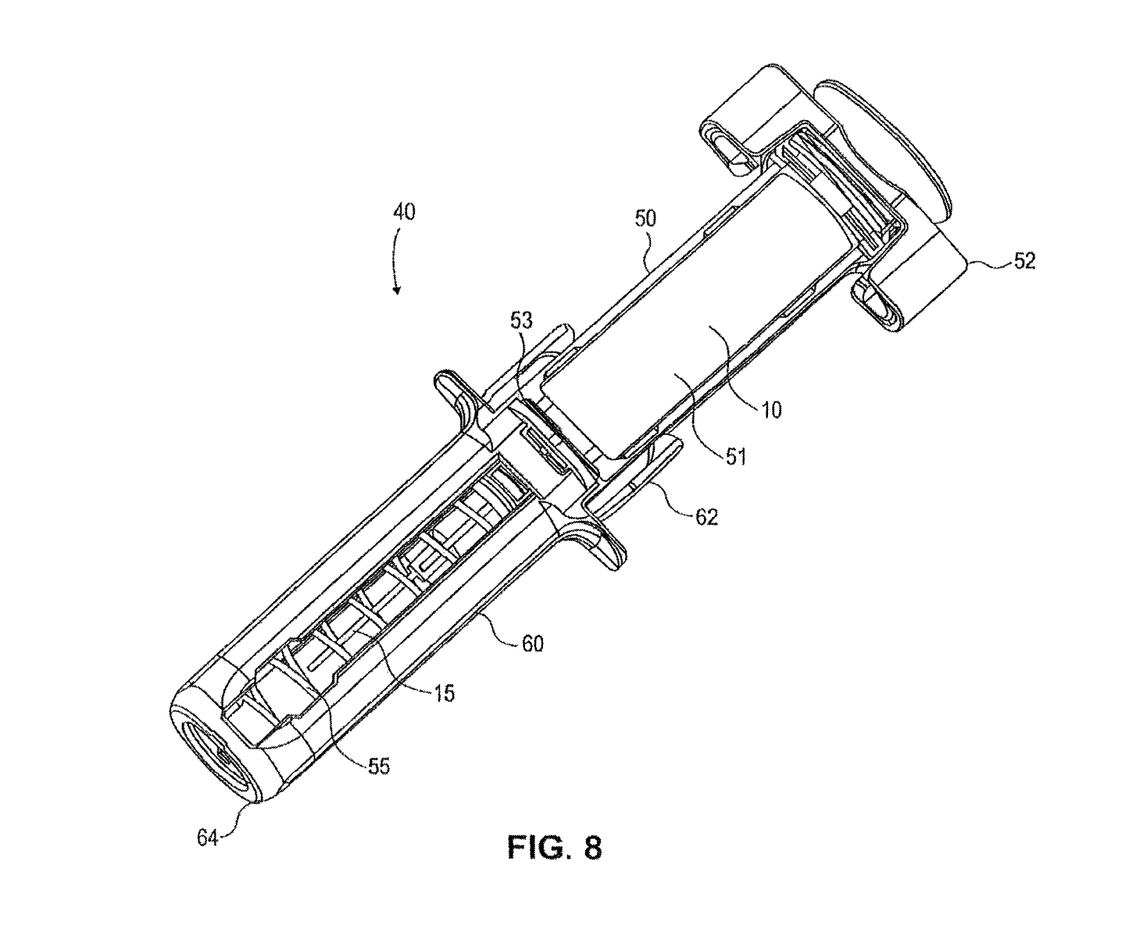
FIG. 8 shows an exemplary embodiment of the device with the shield in the extended position.

The syringe 10 is housed inside the needle guard 40 wherein the needle guard 40 is preferably a passive needle guard (FIG. 1). Safety shield devices generally function, by covering the needle with a rigid cylindrical shield that surrounds the needle and projects far enough beyond the distal tip of the needle so as to prevent a user's finger from coming in contact with the needle tip (FIG. 8). To prevent a user from forgetting to deploy the safety shield, preferred safety devices operate passively or automatically by providing a mechanism that initiates and physically executes the shielding of the needle after the injection has been completed. The passive needle guard 40 generally comprises a body 50 for receiving and holding the syringe 10, a shield 60 slidably attached to the body 50, and a spring mechanism 55 (FIG. 8). Both the body 50 and the shield 60 are generally molded from plastic, such as, polypropylene, k-resin, or polycarbonate, or the like. In a preferred embodiment, the body 50 and the shield 60 are substantially clear to facilitate observation of the syringe 10 therein. Alternatively, the body 50 and the shield 60 may be translucent or opaque, and may be colored, such as a latex color, a flesh tone, or a primary color. The body 50 may comprise opposing side rails defining two elongate openings or windows 51 extending at least partially between a proximal end 52 and a distal end 53 of the body 50 (FIG. 8).

Figure 6:
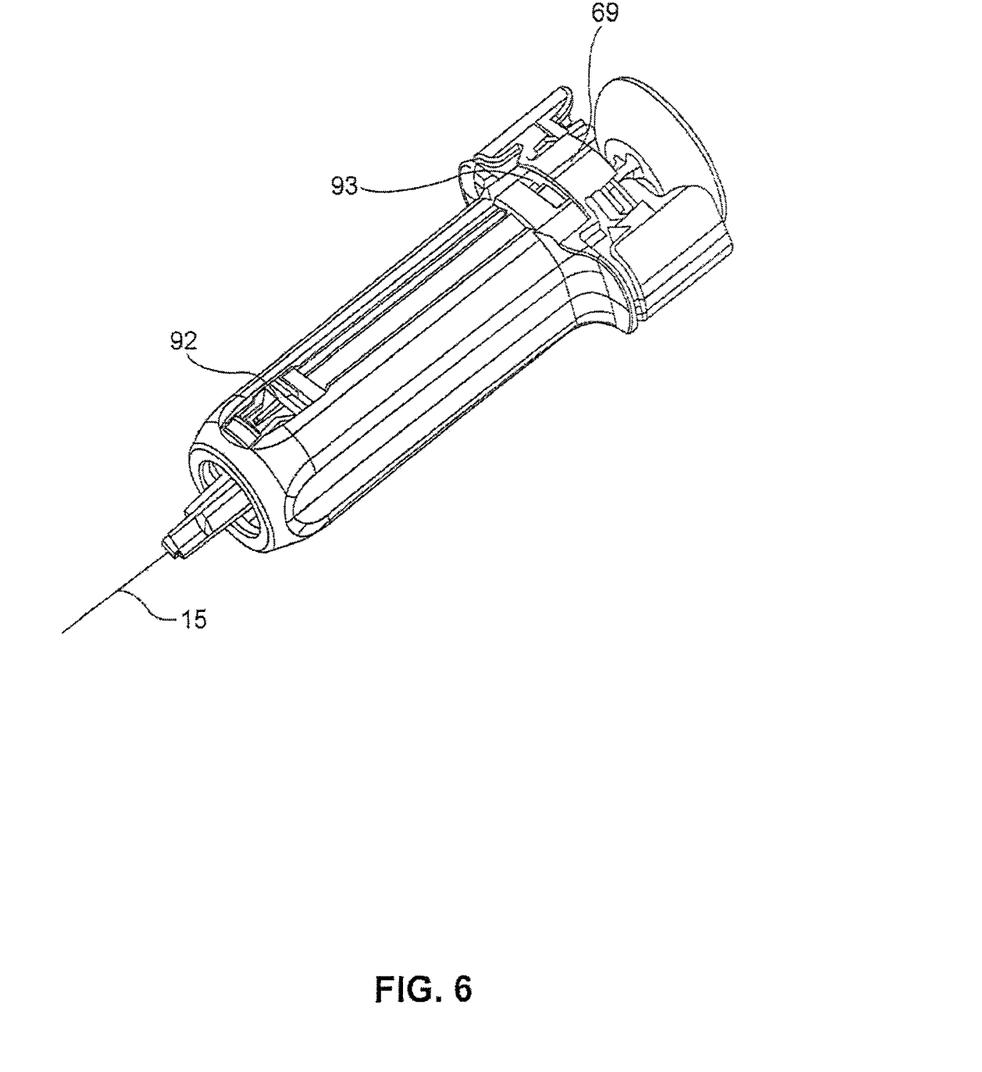
FIG. 6 shows an exemplary embodiment of the device showing the plunger in the distal position and an administration needle coupled to the distal end of the syringe.

The shield 60 is a tubular member adapted to slidably fit on the body 50 and has a proximal end 62 and a distal end 64 (FIGS. 1 and 8). In a preferred embodiment, one or more trigger fingers 66 extend proximally from the proximal end 62 of the shield 60 (FIG. 7). The trigger fingers 66 may include a first catch 68 that is configured to engage a second catch 58 on the proximal end 52 of the body 50 of the needle guard 40. Engagement between the first catch 68 and the second catch 58 retains the shield 60 in a first, retracted position. This latched configuration is further secured by an angled orientation of the latch surfaces, which when combined with the force of the spring 55 urging these surfaces against each other, places a component of force on the trigger fingers 66 directed toward the centerline. Preferably, the one or more trigger fingers 66 are elongate fingers having a proximal tip 67 that is engageable by the thumb pad 36 of the plunger 30 as it is depressed to axially compress and deflect the one or more trigger fingers 66 radially outwardly, as is discussed further below. In a preferred embodiment, the shield 60 further includes an anti-rotation tab 69 which extends proximally from the proximal end 62 (FIGS. 2 and 6). The anti-rotation tab 69 interacts with the flange 18 of the syringe 10 and prevents rotation of the syringe 10. Once the needle guard 40 has been activated, the anti-rotation tab 69 is no longer in proximity to the flange 18 and the syringe can be rotated as desired.

The passive needle guard 40 also includes a spring mechanism 55 coupled to the body 50 and the shield 60 for biasing the shield 60 towards an extended position when the trigger fingers 66 are deflected radially (FIG. 8).

Figure 3:
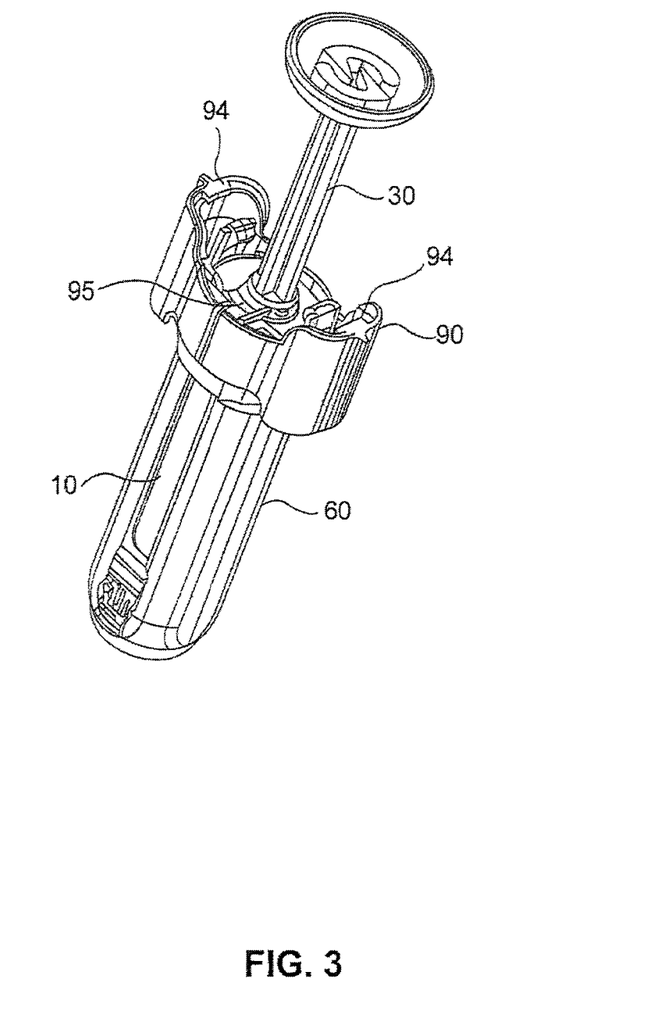
FIG. 3 shows an exemplary embodiment wherein the clip is attached to the proximal portion of the needle guard and the plunger is retracted fully in the proximal direction.
Figure 4:
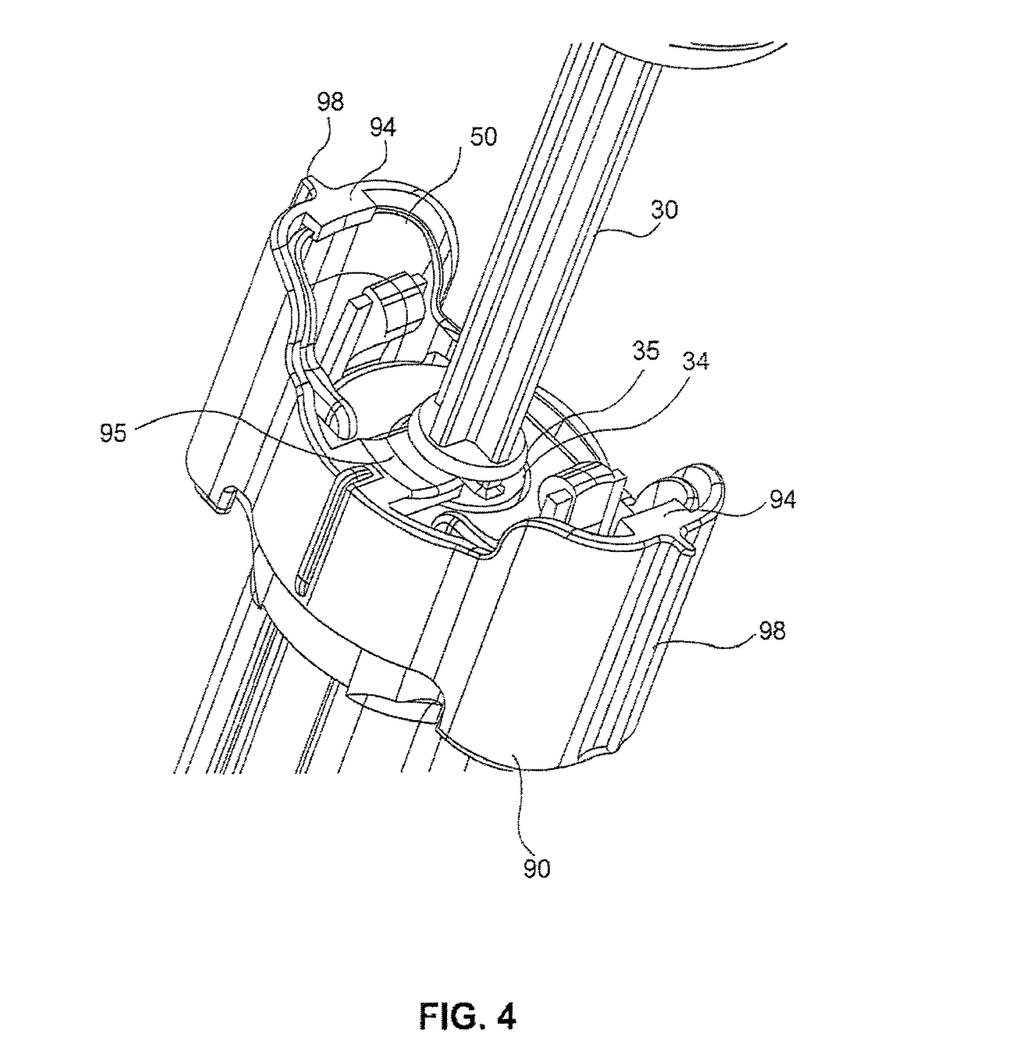
FIG. 4 shows an exploded view of the proximal portion of the device shown in FIG. 3.

The clip 90 is removably coupled with the needle guard 40. The clip 90 can include a tab 95 that creates a physical barrier to removal of the plunger from the needle guard safety device 5 (FIGS. 3 and 4). When the plunger is moved proximally, the tab 95 on the clip 90 prevents a user from accidentally removing the plunger 30 (FIG. 3).

To prevent the relative motion of the safety shield 60 during the steps of reconstitution, the clip 90 retains the shield in the retracted position through the interaction of one or more extensions 94, 96 disposed on the distal and proximal portions of the clip 90 that interact with the shield 60 and body 50 of the needle guard 40 (FIGS. 1 and 4). In a preferred embodiment, the proximal extensions 94 extend axially from the clip 90 and are removably coupled with a proximal portion of the body 50. The distal region of the clip 90 preferably includes one or more distal extensions 96 that are removably coupled with the proximal end 62 of the shield 60. The interaction of the extensions 94, 96 with the shield and body prevent the movement of the shield distally with respect to the body. Therefore, even if the trigger fingers 66 are triggered during reconstitution, the shield cannot transition to the second, extended position and instead remains in the retracted position. In a most preferred embodiment, the extensions 94, 96 retain the body and shield in a slightly closer position than the trigger fingers 66 would on their own. This arrangement facilitates the relatching of the trigger fingers 66 following the reconstitution process as discussed below.

In an alternative embodiment, the clip 90 can be configured to interact with the distal end of the needle guard 40 to retain the shield 60 and body 50 in the retracted position when the clip 90 is attached. In this embodiment, the extensions 94, 96 of the clip 90 can be configured to engage (1) the distal end 64 of the shield 60 and (2) the body 50 slightly proximal of a catch 92 disposed near the distal end 53 of the body 50.

In a preferred embodiment, the clip 90 includes a pair of opposing ribs 98 that extend laterally from the sides of the clip 90. The ribs 98 are designed to facilitate removal of the clip 90 following the reconstitution step as discussed further below.

The syringe 10 can be used to administer a lyophilized or concentrated drug to a patient. The lyophilized drug or concentrated drug may be of any type known to those of skill in the art. Preferably, the lyophilized or concentrated drug is stored in a vial 200 or container such as a glass vial (FIG. 1). The vial 200 may include a cover such as a rubber stopper, septum, or cap that can be penetrated by a needle. In a preferred embodiment, the vial 200 is made of a substantially clear glass so that the user can ensure that the diluent and lyophilized drug have been properly and fully mixed.

Assuming that the syringe is pre-filled with a diluent, the steps of reconstituting the drug and administering it into the patient would be to first insert the reconstitution or first needle 8 into the drug vial 200. The plunger 30 is then advanced distally to expel the diluent from the syringe 10 into the drug vial 200.

If the syringe is not pre-filled with the diluent, the first step in the process would be to aspirate diluent into the syringe from a vial or other source of the desired diluent. All other steps in the process would proceed as described above.

It is at this point that the problems with existing safety devices would arise, since advancing the plunger 30 to expel the diluent in the drug vial 200 would trigger the safety shield mechanism of existing safety devices. With the shield now covering the distal end of the device, the rest of the reconstitution steps would be impossible to perform and, additionally, the injection needle would not be accessible in order to inject the patient.

The clip 90 prevents the shield from transitioning to the extended position. Specifically, the extensions 94, 96 disposed on the distal and proximal portions of the clip 90 interact with shield 60 and body 50 such that the shield is retained in the first, retracted position.

The plunger 30 can then travel the full stroke to empty the syringe contents during reconstitution. Even though the safety shield mechanism will have been triggered (i.e. the thumb pad 36 will contact the trigger fingers 66), the shield 60 will not advance to the shielded position because the interaction of the extensions 94, 96 on the clip 90 maintain the shield in the first, retracted position. Because the trigger fingers 66 have an elastic force urging them back into the latched position, the latch mechanism is reversible if the shield 60 has not moved forward. When the plunger 30 is pulled proximally to draw the drug mixture from the vial 200 into the syringe 10, the trigger fingers 66 will relatch themselves against the second catch 58 on the body 50 so that the needle guard 40 is able to trigger the next time the plunger 30 is advanced sufficiently distally (FIG. 6).

After the drug has been dissolved in the diluent, the plunger 30 is withdrawn proximally, pulling the drug mixture into the syringe 10 (FIG. 3). In a preferred embodiment, a circumferential rib 35 on the distal end 34 of the plunger 30 interferes with the tab 95 on the clip 90 preventing the full withdrawal of the plunger 30, so that users will not inadvertently and surprisingly remove the stopper 20 from the syringe 10 and expose the drug to a non-sterile environment (FIG. 4). Preferably, the needle 8 used for reconstitution is replaced with an injection needle 15 having a Luer fitting (FIG. 6). The anti-rotation tab 69 on the proximal end of the shield prevents rotation of the syringe within the needle guard. Preventing rotation of the syringe facilitates removal and coupling of needles or other components to the Luer lock. The clip 90 is then removed in order to administer the medication. The medication is now ready for injection into the patient and the needle guard 40 should deploy in the normal manner after the medication has been injected into the patient.

As discussed above, the thumb pad 36 of the plunger 30 is sized and shaped to displace the trigger fingers 66 laterally away from the latched position that connects them to the body 50 to an unlatched position that substantially disconnects them from the body 50 when the plunger is advanced sufficiently far forward distally, preferably far enough forward that the contents of the syringe 10 are expelled, but before the plunger 30 is arrested by the stopper 20 reaching the distal end of the syringe 10 (FIGS. 7 and 8). As the medication is being injected into the patient, the plunger 30 will displace the trigger fingers 66 causing the force of the spring 55 to move the shield 60 forward preventing the trigger fingers 66 from relatching and initiating the deployment of the safety shield 60. The dotted lines in FIG. 7 depict the movement of the trigger fingers 66 from the latched position to the unlatched position.

After the plunger 30 is fully advanced and the safety shield mechanism has been released, the shield 60 is either moved distally relative to the syringe 10 and needle 15 or the syringe 10 and needle 15 are moved proximally with respect to the shield 60. Passive or automatic deployment of the safety shield 60 is accomplished by way of the compression spring 55 pushing the shield 60 distally and/or the syringe 10 and needle 15 proximally. The spring force is released to the shield 60 and body 50 when the trigger fingers 66 are displaced from the latch configuration. The spring 55 is of sufficient size to move the shield 60 far enough to shield the needle 15 from the user (FIG. 8). In a preferred embodiment, a locking mechanism holds the shield in the extended position. The locking mechanism may comprise, for example, a set of cooperating detents or catches 92, 93 on the shield 60 and body 50 that maintain the shield in the extended position (FIG. 6). Regardless of the relative motion of the safety shield 60, what is common to all devices is that the safety shield 60 is actuated after the plunger has been advanced to empty the syringe contents.

Although preventing the shield from deploying or moving distally over the syringe has been described, it is understood that the present invention would also apply to devices that move the syringe and needle proximally.

While the invention is susceptible to various modifications, and alternative forms, specific examples thereof have been shown in the drawings and herein described in detail. It should be understood, however, that the invention is not to be limited to the particular forms or methods disclosed, but to the contrary, the intention is to cover all modifications, equivalents, and alternatives falling within the spirit and scope of the appended claims.

What is claimed is:

1. A protective system for a medical device, comprising:
a needle guard comprising:
   a shield having a proximal end and a distal end;
   a body having a proximal end and a distal end;
   one or more trigger fingers disposed on the shield, the one or more trigger fingers configured to, in a latched position, maintain the shield in a first, retracted position, the trigger fingers being displaceable from the latched position; and
   a spring configured to bias the shield from the first, retracted position to a second, extended position when the one or more trigger fingers are displaced from the latched position; and
a clip removably coupled with the needle guard, the clip comprising one or more extensions configured to interact with at least one of the shield and the body to retain the shield in the first, retracted position when the one or more trigger fingers are displaced from the latched position,
wherein the clip must be removed in order for the shield to be deployed.

2. The protective system of claim 1, wherein the one or more trigger fingers comprise a first catch, and wherein the body comprises a second catch, the first catch configured to engage the second catch to maintain the shield in a first, retracted position.

3. The protective system of claim 1, wherein the one or more extensions of the clip are located at a proximal end of the clip, and wherein the one or more extensions of the clip interact with a proximal end of the shield and a proximal end of the body to retain the shield in the first, retracted position.

4. The protective system of claim 1, wherein the one or more extensions of the clip comprise two or more extensions, one of the two or more extensions being located at a proximal end of the clip and another one of the two or more extensions being located at a distal end of the clip, and wherein the two or more extensions of the clip interact with a proximal end of the shield and a proximal end of the body to retain the shield in the first, retracted position.

5. The protective system of claim 1, further comprising a locking mechanism.

6. The protective system of claim 5, wherein the locking mechanism comprises a first catch disposed on the shield and a second catch disposed on the body, and wherein when the shield is in the second, extended position, the first catch and the second catch cooperate such that the shield cannot be returned to the first, retracted position.

7. The protective system of claim 1, further comprising a syringe removably coupled with the needle guard.

8. The protective system of claim 7, wherein the syringe is received within the body, the syringe comprising a barrel having a proximal end and a distal end and a plunger slidably coupled with the barrel.

9. The protective system of claim 8, wherein the one or more trigger fingers are displaced by the plunger as the plunger advances distally against the one or more trigger fingers.

10. The protective system of claim 8, wherein the one or more trigger fingers return to the latched position when the plunger is withdrawn proximally and the clip is coupled to the shield and the body.

11. The protective system of claim 8, wherein the plunger comprises a thumb pad, and wherein the one or more trigger fingers are displaced by the thumb pad when the plunger advances distally.

12. The protective system of claim 8, wherein the distal end of the barrel comprises a luer fitting.

13. The protective system of claim 8, wherein the clip further comprises a clip tab configured to interact with the plunger such that the plunger cannot be removed from the syringe barrel when the clip is coupled to the shield and the body and the plunger is moved proximally.

14. The protective system of claim 8, wherein the barrel includes a diluent therein.

15. The protective system of claim 7, wherein the syringe further comprises a flange and the shield comprises a tab, and wherein the flange and the tab are configured such that the syringe cannot rotate when the shield is in the first, retracted position.

* * * * *